United States Patent
Martinelli et al.

(10) Patent No.: US 12,195,721 B2
(45) Date of Patent: Jan. 14, 2025

(54) DEVICE FOR PRODUCING GLOBULES OF ADIPOSE TISSUE

(71) Applicant: Theralip SA, Lugano (CH)

(72) Inventors: Paolo Antonio Martinelli, Pazzallo (CH); Franco Ruffa, Lecco (CH); Daniele Nicolis, Lopagno (CH); Igor Sergio Laerte Stefanini, Cadro (CH); Agatino Christian Tavilla, Agno (CH); Roberto Robortella, Odogno (CH)

(73) Assignee: THERALIP SA, Lugano (CH)

( * ) Notice: Subject to any disclaimer, the term of this patent is extended or adjusted under 35 U.S.C. 154(b) by 1182 days.

(21) Appl. No.: 16/965,226

(22) PCT Filed: Jan. 22, 2019

(86) PCT No.: PCT/EP2019/051453
§ 371 (c)(1),
(2) Date: Jul. 27, 2020

(87) PCT Pub. No.: WO2019/145276
PCT Pub. Date: Aug. 1, 2019

(65) Prior Publication Data
US 2020/0347341 A1  Nov. 5, 2020

(30) Foreign Application Priority Data

Jan. 25, 2018  (CH) .......................................... 90/18
Jan. 25, 2018  (IT) ......................... 102018000001908

(51) Int. Cl.
C12M 1/33  (2006.01)
C12M 1/00  (2006.01)
C12M 1/36  (2006.01)
C12N 5/077  (2010.01)

(52) U.S. Cl.
CPC ............ C12M 45/02 (2013.01); C12M 29/00 (2013.01); C12M 41/48 (2013.01); C12N 5/0653 (2013.01)

(58) Field of Classification Search
CPC ...... C12M 45/02; C12M 29/00; C12M 41/48; C12N 5/0653; C12N 2521/00; A61K 35/35
See application file for complete search history.

(56) References Cited

U.S. PATENT DOCUMENTS

| | | | |
|---|---|---|---|
| 5,079,160 A | 1/1992 | Lacy et al. | |
| 6,321,642 B1 * | 11/2001 | Ou-Young | A23P 20/25 99/450.6 |
| 2015/0231641 A1 | 8/2015 | Tremolada | |
| 2015/0374888 A1 | 12/2015 | Divringi et al. | |
| 2016/0361476 A1 | 11/2016 | Maggiolo et al. | |

FOREIGN PATENT DOCUMENTS

| | | |
|---|---|---|
| WO | 2009/073724 A1 | 6/2009 |
| WO | 2015/140737 A1 | 9/2015 |

OTHER PUBLICATIONS

Bahal, S.M. and Romansky, J.M., 2002. Spalling and sorption of tubing for peristaltic pumps. Pharmaceutical development and technology, 7(3), pp. 317-323. (Year: 2002).*
International Search Report issued in corresponding International Patent Application No. PCT/EP2019/015453 dated Mar. 21, 2019.

* cited by examiner

Primary Examiner — Christopher M Babic
Assistant Examiner — Masudur Rahman
(74) Attorney, Agent, or Firm — TROUTMAN PEPPER HAMILTON SANDERS LLP

(57) ABSTRACT

A device for producing globules of adipose tissue, comprising a service unit and a single-use kit which may be housed in the service unit, the single-use kit comprising a working chamber, a circuit for introducing an adipose tissue sample into the working chamber, a circuit for drawing globules of adipose tissue from the working chamber, a circuit for introducing a solution for washing the tissue sample into the working chamber, and a size-reducing circuit which connects an exit route of the working chamber to an entry route of the working chamber, the service unit having an electronic controller and a means for the forced circulation of the adipose tissue sample through the size-reducing circuit.

11 Claims, 5 Drawing Sheets

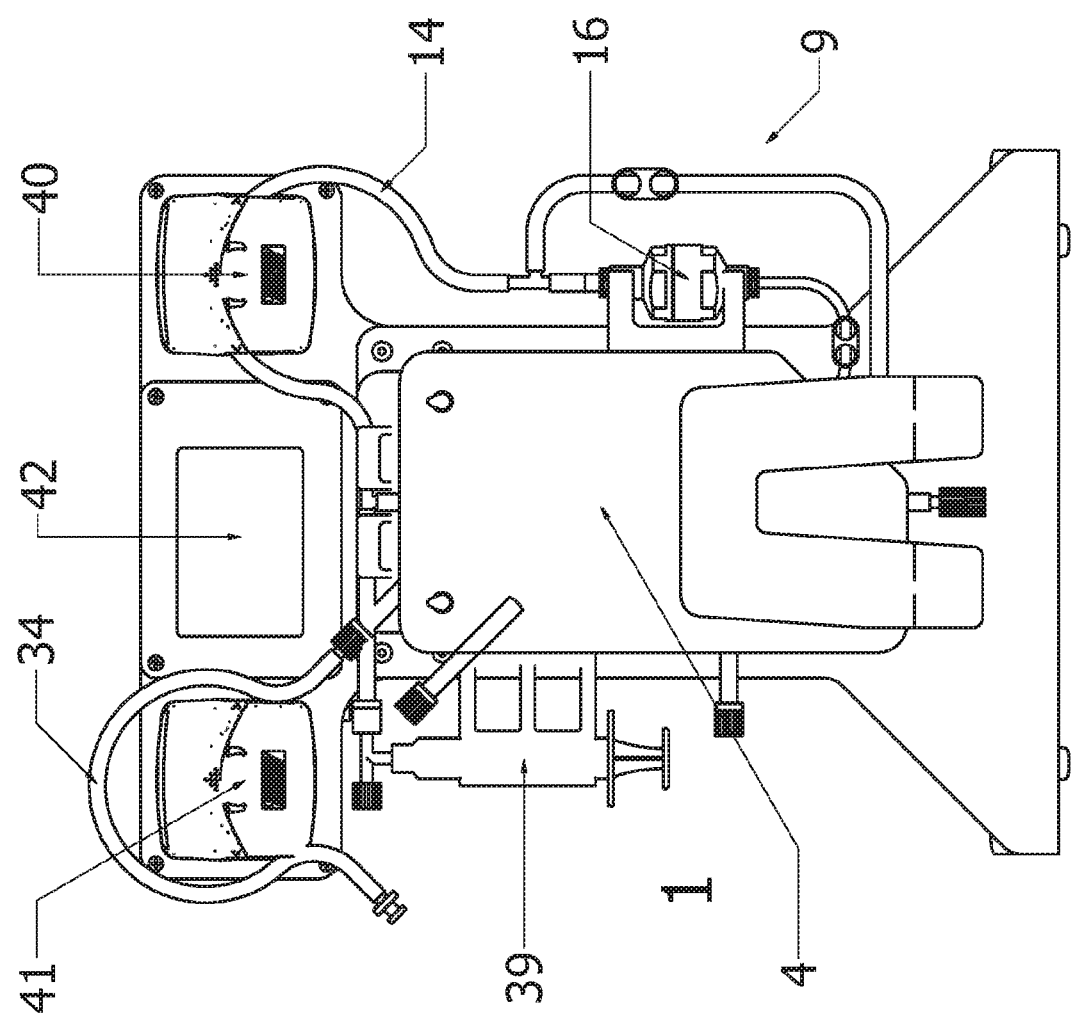

DEVICE FOR PRODUCING GLOBULES OF ADIPOSE TISSUE

CROSS REFERENCE TO RELATED APPLICATION(S)

This is a U.S. National Phase Application under 35 U.S.C. § 371 of International Patent Application No. PCT/EP2019/051453, filed Jan. 22, 2019, which claims priority of Italian Patent Application No. 102018000001908, filed Jan. 25, 2018 and Swiss Patent Application No. 00090/18 filed Jan. 25, 2018. The entire contents of which are hereby incorporated by reference.

FIELD OF THE INVENTION

The present invention relates to a device for producing globules of adipose tissue.

BACKGROUND

In the current state of the art, extraction systems of mesenchymal stromal cells are known that are based on the use of enzymes capable of digesting the adipose tissue and releasing the cells retained therein.

These extraction systems are unsatisfactory, in particular for that which concerns the survival rate of the extracted cells following cryopreservation.

A portable device for producing globules of adipose tissue is also known from patent application US 2015/0231641 which provides a working chamber into which small size-reducing spheres are placed that are activated by the operator by means of manual agitation.

Obviously in this case the yield of the device is closely linked to the ability and experience of the operator.

SUMMARY

The technical task which the present invention sets itself is, therefore, to create a device for producing globules of adipose tissue which makes it possible to eliminate the technical drawbacks complained of in the prior art.

Within the scope of this technical task, an object of the invention is to provide a device for producing globules of adipose tissue capable of considerably improving the reuse of the population of stem cells present in the globules of adipose tissue.

A further object of the invention is to provide a device for producing globules of adipose tissue that is able to operate in a completely automated manner without therefore requiring the presence of an operator with specific skills.

The technical task, as well as other objects, are obtained according to the present invention through the creation of a device for producing globules of adipose tissue, characterized in that it comprises a service unit and a single-use kit which may be housed in said service unit, said single-use kit comprising a working chamber, a circuit for introducing an adipose tissue sample to be treated into said working chamber, a circuit for drawing globules of adipose tissue from said working chamber, a circuit for introducing a solution for washing said tissue sample into said working chamber, and a size-reducing circuit which connects an exit route of said working chamber to an entry route of said working chamber, said service unit having an electronic controller and a means for the forced circulation of said tissue sample through said size-reducing circuit.

The device for producing globules of adipose tissue according to the invention is advantageously able to eliminate residues, in particular oil and blood residues, from the tissue sample, for example the adrenaline and lidocaine used in the liposuction procedure, and reduce the latter into small globules, making the population of stem cells contained therein more easily accessible and functional for the purposes of the subsequent re-infusion or cryopreservation.

Preferably said working chamber is formed by a flexible bag.

Preferably said kit also comprises a circuit for discharging the scraps of the treated sample.

Preferably said size-reducing circuit comprises a flexible tube.

Preferably said forced circulation means comprise a primary peristaltic pump coupled to said flexible tube.

Preferably said size-reducing circuit comprises a mechanical size-reducing unit that does not require a supply of electricity to operate.

In a possible embodiment, said mechanical size-reducing unit comprises a series of spiral blades with a decreasing pitch and/or filters with crossed slots.

Preferably said kit comprises a circuit for bypassing said size-reducing circuit. Preferably said circuit for introducing a solution for washing comprises a flexible tube.

Preferably said service unit comprises an auxiliary peristaltic pump coupled to said flexible tube of said circuit for introducing a washing solution.

Preferably said service unit comprises a user interface.

Preferably said interface comprises at least one selector of the time and speed of activation of said forced circulation means.

Preferably said interface comprises a selector of the time and speed of activation of said primary peristaltic pump and a selector of the time and speed of activation of said auxiliary peristaltic pump.

In a possible embodiment said service unit comprises a plate-like weight-bearing frame having a flat horizontal rest wall and a flat, slightly inclined vertical wall provided with a support for positioning said working chamber, supports for positioning said drawing circuit and said size-reducing circuit at the opposite sides of said working chamber, a support for positioning said interface above said working chamber, and supports for positioning said primary peristaltic pump and auxiliary peristaltic pump at the opposite sides of said interface.

Advantageously the device for producing globules of adipose tissue according to the invention is limited to reducing the size of the globules of adipose tissue to the desired dimensions, preferably from 0.2 to 0.8 mm, using a purely mechanical trituration process obtained by passing the adipose tissue through orifices of gradually smaller diameters.

This approach helps to increase the survival rate of the cells contained in the globules of adipose tissue after cryopreservation or re-infusion.

Advantageously the device for producing globules of adipose tissue according to the invention uses a low-cost single-use kit which is structurally simple and easy to use, and completely passive because not powered electrically.

Advantageously the device for producing globules of adipose tissue according to the invention ensures the uniformity and reproducibility of the results thanks to automated treatment protocols and procedures.

Advantageously the device for producing globules of adipose tissue according to the invention ensures the necessary sterile conditions allowing a closed-circuit working process wherein the preparation and loading of the kit can occur under a laminar flow hood.

BRIEF DESCRIPTION OF THE DRAWINGS

Further characteristics and advantages of the invention will more fully emerge from the description of a preferred but not exclusive embodiment of the device for producing globules of adipose tissue according to the invention, illustrated by way of indicative and non-limiting example in the accompanying figures of the drawings, in which:

FIG. 5 shows a front view of the single-use kit housed inside the service unit.

DETAILED DESCRIPTION OF THE DRAWINGS

Figure 1:
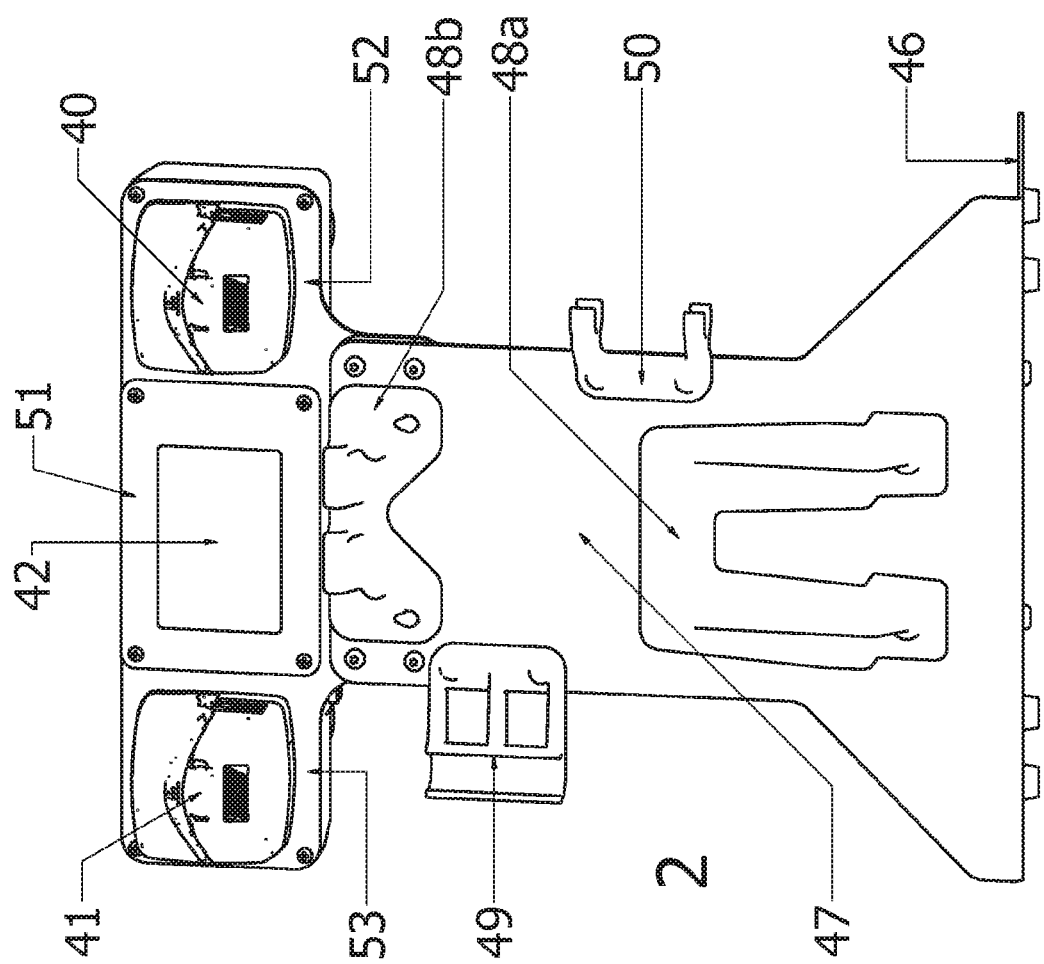
FIG. 1 shows a front view of the service unit.
Figure 2:
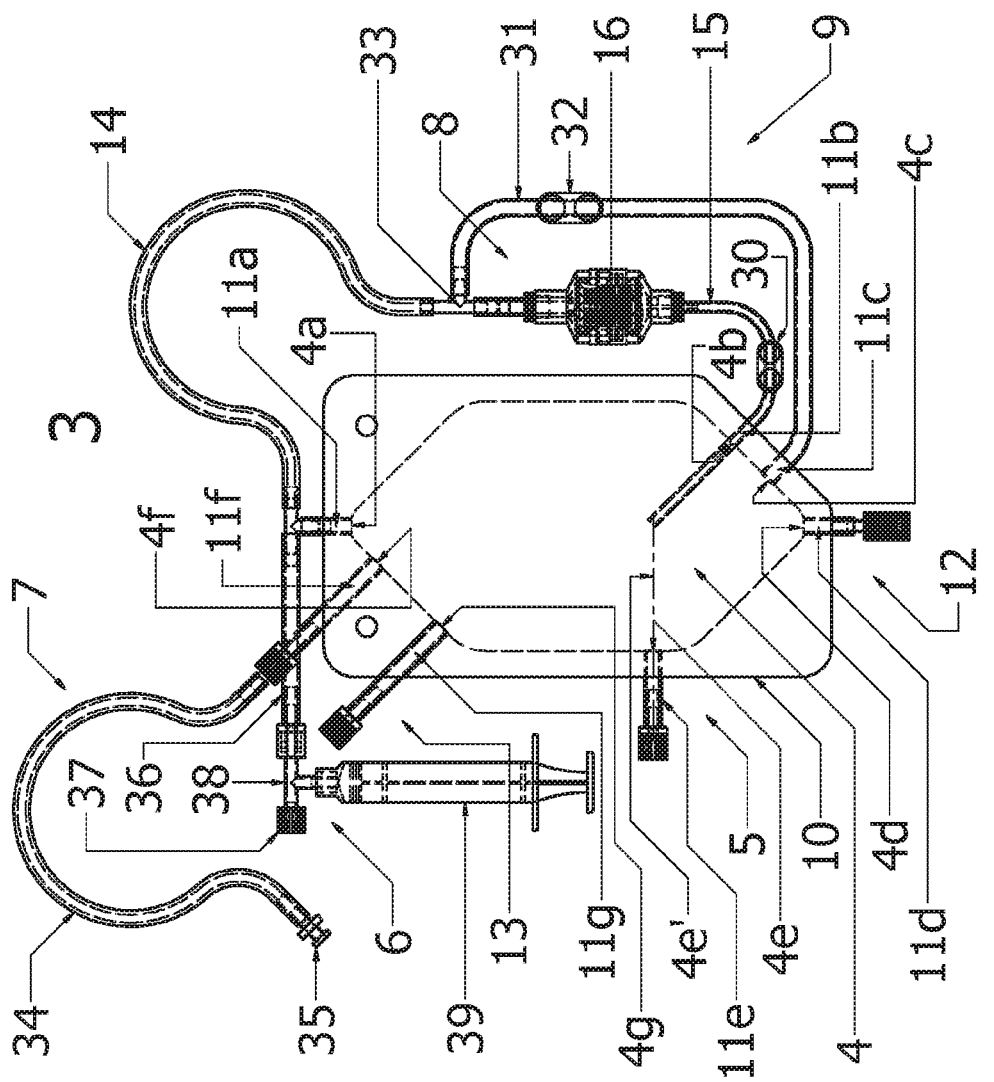
FIG. 2 shows a front view of the single-use kit.
Figure 3:
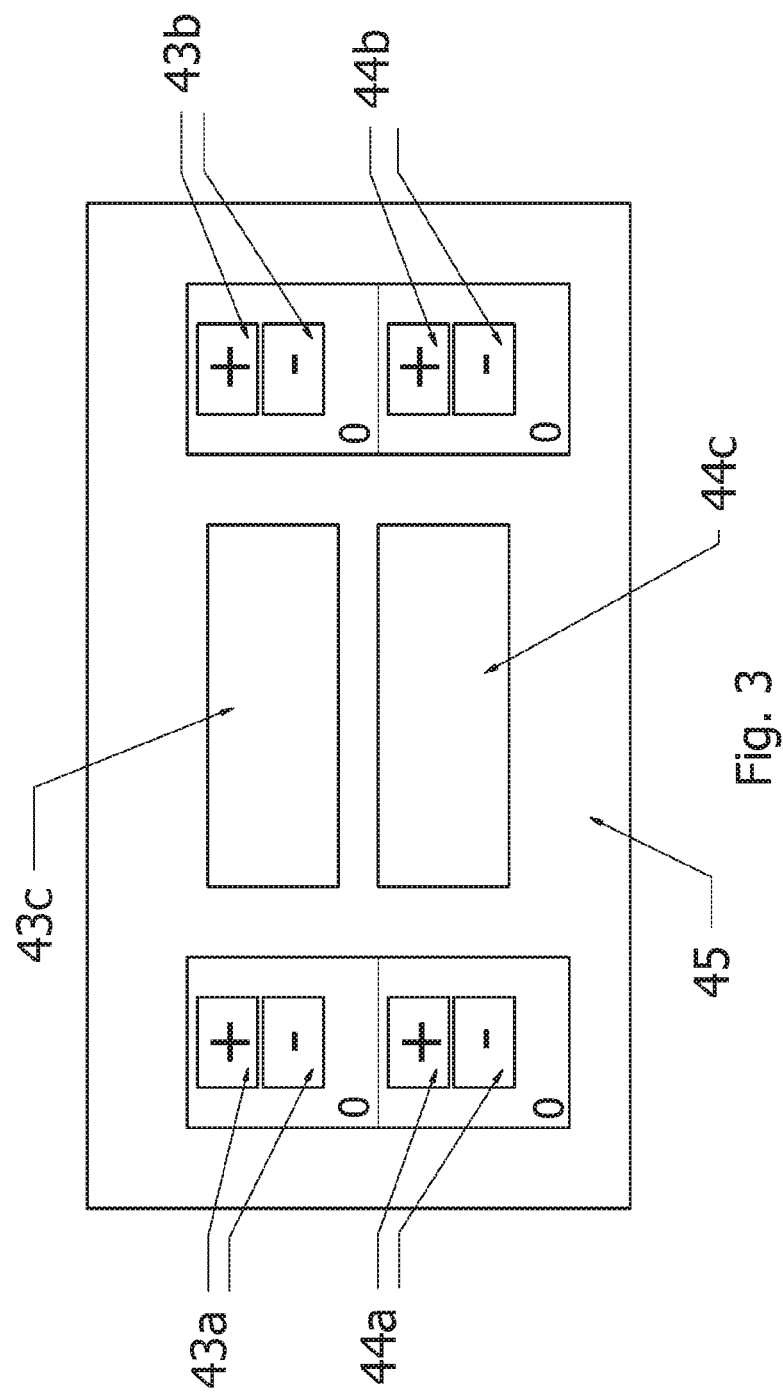
FIG. 3 shows a detailed view of the graphic user interface of the service unit.
Figure 4:
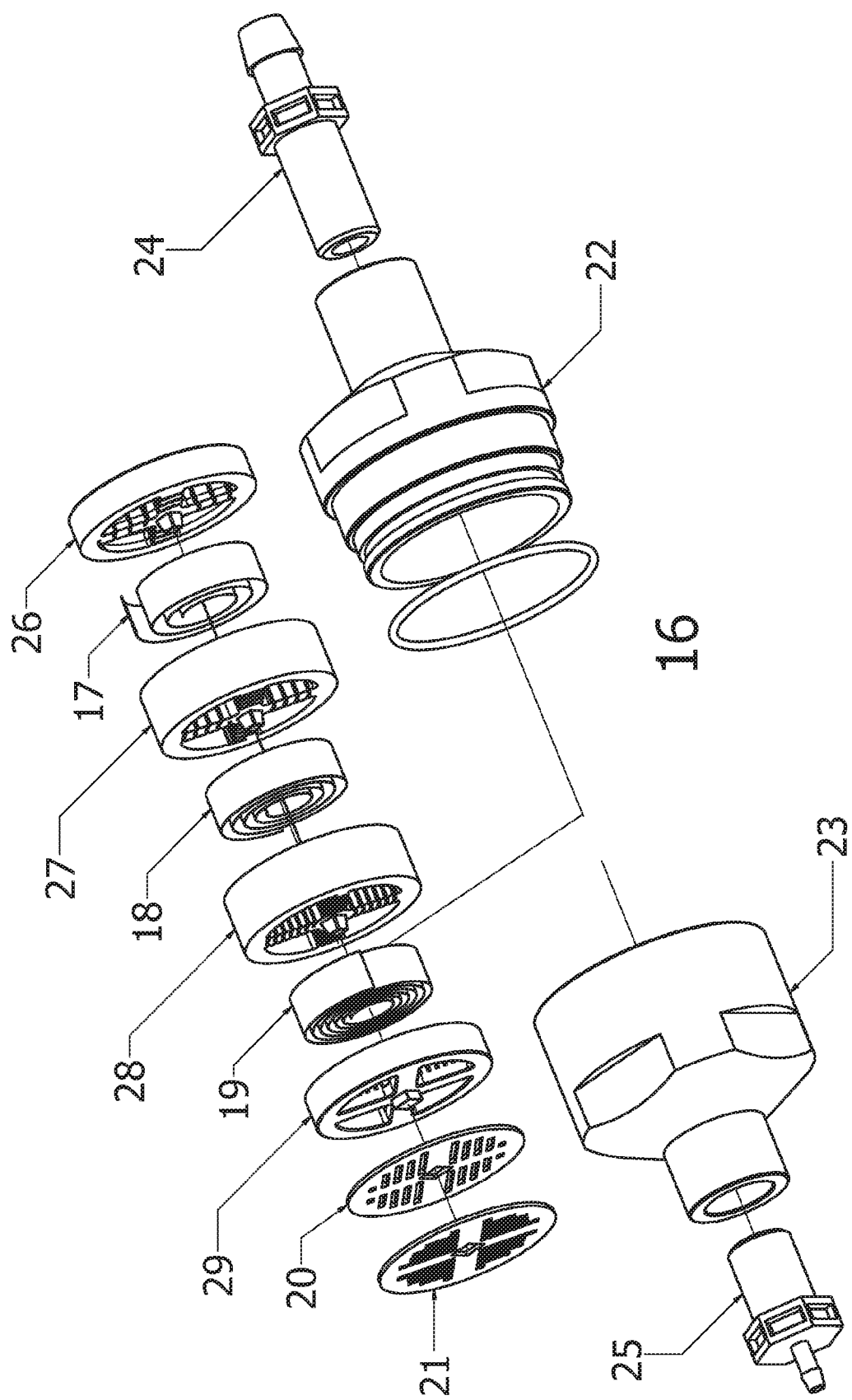
FIG. 4 shows an exploded view of the size-reducing unit.

With reference to the figures mentioned, a device for producing globules of adipose tissue is denoted in its entirety by reference number 1.

The adipose tissue used in most applications is human adipose tissue.

The device 1 comprises a service unit 2 and a single-use kit 3 which may be housed in the service unit 2.

The single-use kit 3 comprises a working chamber 4, a circuit 5 for introducing a tissue sample to be treated into the working chamber 4, a circuit 6 for drawing the globules of adipose tissue produced from the working chamber 4, a circuit 7 for introducing a solution for washing the tissue sample into the working chamber 4, and a size-reducing circuit 8 which connects an exit route 4a of the working chamber 4 to an entry route 4b of the working chamber 4.

The kit 3 also comprises a circuit 12 for discharging the scraps of the treated sample. The kit 3 finally comprises a bypass circuit 9 for bypassing the size-reducing circuit 8. The working chamber 4 is formed by a flexible bag 10.

In particular the bag 10 is constituted by two suitably shaped sheets peripherally welded together.

Between the welded edges of the two sheets, one end of connection fittings 11a, 11b, 11c, 11d, 11e, 11f, 11g is arranged to connect the working chamber 4 to the various circuits of the kit 3.

The fitting 11a, comprising in particular a tube having a single entry and double exit, connects the exit route 4a of the working chamber 4 to the drawing circuit 6 and size-reducing circuit 8.

The fitting 11b, comprising in particular a smaller lumen-shaped tube with a single entry and single exit, connects the entry route 4b of the working chamber 4 to the size-reducing circuit 8.

The fitting 11b extends substantially inside the working chamber 4 along a direction which intersects the prolongation 4e inside the working chamber 4 of an entry route 4e of the adipose tissue sample to be treated.

The fitting 11c, comprising in particular a tube having a single entry and single exit, connects the entry route 4c of the working chamber 4 to the bypass circuit 9.

The fitting 11d, comprising in particular a tube with a single entry and single exit, connects the exit route 4d of the working chamber 4 to the discharge circuit 12.

The fitting 11e, comprising in particular a tube with a single entry and double exit, connects the entry route 4e of the working chamber 4 to the circuit 5 for introducing the adipose tissue sample to be treated.

The fitting 11f, comprising in particular a tube having a single entry and single exit, connects the entry route 4f of the working chamber 4 to the circuit 7 for introducing a solution for washing.

Eventually the fitting 11g, comprising in particular a tube having a single entry and single exit, connects the entry route 4g of the working chamber 4 to an auxiliary circuit 13.

The bag 10 can be made of PVC for medical applications and have a certain capacity, for example 200 ml.

The size-reducing circuit 8 comprises a flexible tube 14, 15 and a mechanical size-reducing unit 16.

The flexible tube 14, 15 comprises a first tube section 14 that connects the exit route 4a of the working chamber 4 to the entry route of the size-reducing unit 16 and a second, lower, lumen-shaped tube section 15 which connects the exit route of the size-reducing unit 16 to the entry route 4b of the working chamber 4.

The mechanical size-reducing unit 16, which does not require electricity for its operation, comprises a series of for example three spiral blades 17, 18, 19 with a decreasing pitch and arranged in cascade fashion to the spiral blades 17, 18, 19, a series for example of two filters 20, 21 with slots crossed at right angles.

In particular the mechanical size-reducing unit 16 comprises a shell 22, 23 with an axial extension, preferably cylindrical and formed by two halves sealedly connected, which encloses the spiral blades 17, 18, 19 and the filters 20, 21.

The shell 22, 23 has at each of its bases a lumen-shaped connection fitting 24, 25 different between them at a respective section of lumen-shaped tube 14, 15 different between them.

The spiral blades 17, 18, 19 and filters 20, 21 are stacked coaxially inside the shell 22, 23.

Suitable spacers 27, 28 are also provided in the shell 22, 23 and are equipped with through openings adapted to mutually separate the spiral blades 17, 18, 19 and a spacer 29 equipped with through openings adapted to separate the last spiral blade 19 from the filters 20, 21.

A further spacer 26 equipped with through openings separates the first spiral blade 17 from the base adjacent to the shell 22,23.

By way of example, the three spiral blades have a pitch of respectively 2 mm, 1.5 mm, 1 mm, while the filters 20, 21 with slots have a smaller width than the pitch of the last spiral blade 29, for example a width equal to 0.8 mm.

The size-reducing circuit 8 also comprises a clamping element 30, for example a tube-restricting clamp acting on the second section of tube 15.

The bypass circuit 9 also comprises a flexible tube 31 equipped with a clamping element 32, for example a tube-restricting clamp.

The flexible tube 31 connects the size-reducing circuit 8 upstream of the size-reducing unit 16 through a three-way fitting 33.

The circuit 5 for introducing the sample to be treated may comprise a flexible tube (not shown) connected to the fitting 11e and equipped with a closure cap (not shown) and a clamping element (not shown), for example a tube-restricting clamp.

The flexible tube of the circuit 5 for introducing the sample to be treated is connectable to a container of the sample to be treated, for example a syringe.

The drawing circuit 6 comprises a flexible tube 36 connected to the fitting 11a and equipped with a closure cap 37 and a connecting element 38, for example a T-shaped manifold.

The flexible tube of the drawing circuit 6 is connectable via the connecting element 38 to a container of globules of adipose tissue, for example a syringe 39.

The circuit 7 for introducing a solution for washing comprises a flexible tube 34 connected to the fitting 11f and equipped with a closure cap 35 and a clamping element (not shown), for example a tube-restricting clamp.

The flexible tube 34 of the circuit 7 for introducing the solution for washing 1s connectable to a container of washing solution (not shown).

The washing solution is for example a saline solution.

The circuit 12 for discharging the washing solution also comprises a flexible tube (not shown) connected to the fitting 11d and equipped with a closure cap (not shown) and a clamping element (not shown), for example a tube-restricting clamp.

The flexible tube of the discharging circuit 12 is connectable to a container of the scrap product, for example a bag.

Advantageously the service unit 2 has an electronic controller (not shown) and means for the forced circulation of the tissue sample through the size-reducing circuit 8.

The forced circulation means comprise a primary peristaltic pump 40 coupled to the flexible tube 14, 15, particularly to an arcuate portion of the first section of tube 14.

The service unit 2 also comprises an auxiliary peristaltic pump 41 coupled to the flexible tube 34 of the circuit 7 for introducing the solution for washing, particularly to an arcuate portion of the flexible tube 34.

The primary peristaltic pump 40 and the secondary peristaltic pump 41 are connected to the electronic controller.

The service unit 2 further comprises a user interface 42 which is also connected to the electronic controller.

The interface 42 comprises at least one selector of the time and speed of activation of said forced circulation means.

More precisely, a selector of the time and speed of activation of the primary peristaltic pump 40 is envisaged, and a selector of the time and speed of activation of the secondary peristaltic pump 41 is envisaged.

The interface 42 is a graphic type, preferably a touch screen display.

Specifically, the touch screen display has ten buttons, with two buttons 43a acting as a selector of the time of activation of the primary peristaltic pump 40, two buttons 43b acting as a selector for the speed of activation of the primary peristaltic pump 40, a button 43c acting as a start and stop of the trituration/washing functions, two buttons 44a acting as a selector of the time of activation of the secondary peristaltic pump 41, two buttons 44b acting as a selector of speed of activation of the secondary peristaltic pump 41, a button 44c acting as a start and stop of the loading of fresh washing solution into the working chamber 4.

The graphic interface 42 is completed by a timer 45 for the display of the time remaining to complete the trituration or washing.

To provide visual feedback of the operation in progress, the background of a button changes color when the same is activated.

The service unit 2 comprises a plate-like weight-bearing frame having a flat horizontal rest wall 46 and a flat, slightly inclined vertical wall 47 provided with a support 48a, 48b for positioning the working chamber 4, a support 49 for positioning the drawing circuit 6 on one side of the working chamber 4, a support 50 for positioning the size-reducing circuit 8 on the opposite side of the working chamber 4, a support 51 for positioning the interface 42 above the working chamber 4, and supports 52, 53 for positioning the primary peristaltic pump 40 and the auxiliary peristaltic pump 41 at the opposite sides of the interface 42.

At the rear, the flat rest wall 46 has a ballast (not shown) in order to increase the stability of the system.

The support 48a, 48b is formed for example by a bottom bracket 48a releasably housing the lower portion of the flexible bag 10 and an upper gripper 48b that releasably clamps the upper portion of the flexible bag 10.

The support 49 is formed for example by a housing which can hold and release the syringe 39 and the support 50 is formed for example by a housing which can hold and release the shell 22, 23 of the size-reducing unit 16.

The supports 51, 52, 53 are instead simply fastening housings, for example by means of screws or bolts, for the peristaltic pumps 40, 41 and the interface 42.

The service unit 2 also comprises an electric power supply (not shown) required to supply electric energy to the active components, in particular a low voltage, direct current power supply, for example a power supply of at least 50 W, 24V.

A typical working session with the device 1 is composed of the following four stages: preparation of the kit 3, loading the kit 3, treating the sample, and extraction of the reduced sample.

The single-use kit 3 is supplied in sterile packaging which should be opened under a laminar flow hood in order to minimize the risk of contamination, in particular, of the internal part of the circuit. For the preparation of the kit 3, it is therefore necessary to prepare all the material necessary for loading the kit in the hood as well as its hermetic closure, i.e. the container of washing solution, the syringe with the sample to be treated, the drawing syringe or batch of syringes 39, and the scrap product container.

Once the material for performing the loading of the kit is prepared in the hood, proceed as follows.

Close the tube of the discharge circuit 12 with the clamp, remove the cap from the tube of the discharge circuit 12 and connect the tube of the discharge circuit 12 to the scrap product collection container with its clamp closed.

Close the tube of the washing circuit 7 with the clamp, remove the cap from the tube of the washing circuit 7 and connect the container with the washing solution.

At this point open the washing circuit 7 and let a quantity flow into the bag, for example approximately equal to that of the tissue that will be treated.

Close the container of the washing solution.

Close the tube of the circuit 5 for introducing the sample with the clamp.

Open the cap of the circuit 5 for introducing the sample, connect the latter to the syringe containing the sample to be treated, and inject the latter into the flexible bag 10.

Close the tube of the circuit 5 for introducing the sample with the clamp, disconnect the loading syringe, close the cap of the tube of the circuit 5 for introducing the sample and open the clamp.

At the end of the indicated operations the kit is sealed, thus it can be removed from the hood and housed in the service unit 2.

Depending on need, the service unit 2 can also be kept under the hood, in this case the kit 3 is housed therein and should be moved into the area envisaged for its use.

In the case of direct use in the operating theatre, all the steps which are envisaged under a laminar flow hood must be carried out in the sterile area of the operating room.

For the correct operation of the system, in particular for that concerning the separation of the lipid and aqueous phases, the service unit 2 and the kit 3 housed therein must be used in a vertical position.

Once the service unit is connected to its own power supply, the treatment of the tissue sample can proceed according to two modes: trituration/washing or washing only.

A third feature of the device makes it possible to load fresh washing solution into the bag 10 for further treatment sessions.

The two modes of trituration/washing are activated with the same button after selecting circuit 8 or 9 by means of the selective opening of the clamp 30 or clamp 32.

In trituration mode, wherein the clamp 30 is open on the size-reducing circuit 8 downstream of the size-reducing unit 16 and the clamp 32 on the bypass circuit 9 is closed, the sample is forced to pass into the size-reducing unit 16 together with the saline solution.

The sample undergoes a subsequent fragmentation in the size-reducing unit 16 thanks to the work of the spiral blades and/or slotted filters present therein.

The difference in the diameters of the entry and exit routes of the size-reducing unit 16 entails a difference in the flow across the same, and a consequent difference in the speed of the fluid exiting the flexible bag 10 and that entering. The difference in speed produces a continuous remixing between the aqueous and lipid phases, which is indispensable for the homogeneity and purity of the final product. At the end of the treatment, the lipid phase will form a suspension over the aqueous phase which can be eliminated by making it flow into the suitable bag for collecting scrap products, after the opening of the respective clamp. The treatment can be repeated, at the discretion of the operator.

For the washing mode, it is necessary to close the clamp 30 downstream of the size-reducing unit 16 and open the other clamp 32. In this case the sample and saline solution are simply recirculated; the adipose tissue is not reduced in size but only washed externally. Also in this case the cycle can be repeated.

For each mode, the speed of the primary peristaltic pump 40 and the duration of the treatment must be set, after which pressing the start button 43c initiates the selected procedure automatically until after the set time has elapsed.

The loading of substances into the working chamber 4 can be carried out in two different ways. In the standard way, a defined amount of saline solution is introduced into the working chamber 4 before starting the trituration/washing or only washing procedure. The standard way is that used in the preliminary phase of the kit's preparation. The washing solution will only be eliminated at the end of the treatment. The second way instead envisages the continuous introduction of saline solution, regulated by the auxiliary peristaltic pump 41, during the washing/trituration or washing procedure. Since the volume of the kit 3 is limited, it will be necessary to keep the clamp on the scrap collection bag open so as to collect the saline solution introduced.

At the end of the treatment the lipid phase spontaneously collects by floating up to the top of the bag 10 and is ready to be retrieved and used. The aqueous phase thereunder can be made to flow into the scrap bag or kept in order to facilitate the subsequent operation for extracting the sample reduced in size.

The extraction takes place by means of the syringe 39 or a batch of syringes 39.

It is sufficient to draw the desired amount of globules of adipose tissue with the syringe 39, remove the syringe 39 and use the extracted product according to need.

In the case where a batch of syringes 39 is used, it is necessary to close the connector of each of them with their cap as soon as they are separated from the kit 3.

The device for producing globules of adipose tissue as conceived herein is susceptible to many modifications and variations, all falling within the scope of the inventive concept; furthermore, all the details are replaceable by technically equivalent elements.

In practice the materials used, as well as the dimensions, can be any according to the needs and the state of the art.

The invention claimed is:

1. A device for producing globules of adipose tissue, comprising
    a service unit and a single-use kit which may be housed in said service unit, said single-use kit comprising:
        a working chamber,
        a circuit for introducing an adipose tissue sample into said working chamber, and
        a circuit for drawing globules of adipose tissue from said working chamber,
    said working chamber is formed by a flexible bag and in that said single-use kit further comprises:
        a washing circuit introducing a saline solution washing said tissue sample into said working chamber,
        a size-reducing circuit which connects an exit route of said working chamber to an entry route of said working chamber, and
        a bypass circuit for bypassing said size-reducing circuit, and recirculating said sample and said saline solution into said working chamber,
    said service unit having an electronic controller and a forced circulator forcing a circulation of said tissue sample through said size-reducing circuit,
    said size-reducing circuit comprising a mechanical size-reducing unit that does not require a supply of electricity to operate, wherein said mechanical size-reducing unit comprises
    a series of spiral blades with a decreasing pitch, arranged in cascade fashion, with a series of filters with crossed slots,
    said size-reducing circuit further comprising a clamping element and a flexible tube comprising a first tube section that connects the exit route of said working chamber to an entry route of said size-reducing unit and a second, lower, lumen-shaped tube section which connects an exit route of said size-reducing unit to the entry route of said working chamber, wherein the first tube section has lumen with a dimension that is different from the dimension of the second, lower, lumen-shaped tube section,
    said bypass circuit also comprising:
        a flexible tube equipped with a clamping element, said flexible tube of said bypass circuit connecting said size-reducing circuit upstream of said size-reducing unit through a three-way fitting,
        a washing mode with said clamping element of said size-reducing circuit closed and said clamping element of said bypass circuit open being provided where said sample and said saline solution are simply recirculated, and
        a trituration mode with said clamping element of said size-reducing circuit open and said clamping element of said bypass circuit closed being provided where said sample is forced to pass into said size-reducing unit together with said saline solution.

2. The device for producing globules of adipose tissue according to claim 1, wherein said single-use kit comprises a circuit discharging the scraps of the treated sample.

3. The device for producing globules of adipose tissue according to claim 1, wherein said forced circulator comprises a primary peristaltic pump coupled with said flexible tube.

4. The device for producing globules of adipose tissue according to claim 1, wherein said washing circuit comprises a flexible tube.

5. The device for producing globules of adipose tissue according to claim 4, wherein said service unit comprises an auxiliary peristaltic pump coupled with said flexible tube of said washing circuit.

6. The device for producing globules of adipose tissue according to claim 1, wherein said service unit comprises a user interface.

7. The device for producing globules of adipose tissue according to claim 6, wherein said interface comprises at least one selector of the time and speed of activation of said forced circulation means.

8. The device for producing globules of adipose tissue according to claim 7, wherein said interface comprises a selector of the time and speed of activation of said primary peristaltic pump and a selector of the time and speed of activation of said auxiliary peristaltic pump.

9. The device for producing globules of adipose tissue according to claim 1, wherein said service unit comprises a plate-like weight-bearing frame having a flat horizontal rest wall and a flat vertical wall provided with a support for positioning said working chamber, supports for positioning said drawing circuit and said size-reducing circuit at the opposite sides of said working chamber, a support for positioning said interface above said working chamber, and supports for positioning said primary peristaltic pump and auxiliary peristaltic pump at the opposite sides of said interface.

10. The device for producing globules of adipose tissue according to claim 1, wherein said size-reducing unit is configured for the production of globules of adipose tissue with a diameter comprised between 0.2 and 0.8 mm.

11. The device for producing globules of adipose tissue according to claim 1, wherein said size-reducing circuit has a terminal with a smaller lumen for entry into said working chamber to accelerate the flow and consequently increase the remixing efficiency in said working chamber.

* * * * *